United States Patent [19]
Bock et al.

[11] 4,353,897
[45] Oct. 12, 1982

[54] PESTICIDAL COMPOSITIONS

[75] Inventors: Klaus-Detlef Bock, Kelsterbach, Fed. Rep. of Germany; Horst Baum, Nairobi, Kenya

[73] Assignee: Hoechst Aktiengesellschaft, Frankfurt am Main, Fed. Rep. of Germany

[21] Appl. No.: 181,982

[22] Filed: Aug. 28, 1980

[30] Foreign Application Priority Data

Aug. 30, 1979 [DE] Fed. Rep. of Germany ....... 2934978

[51] Int. Cl.$^3$ ..................... A01N 57/00; A01N 57/26
[52] U.S. Cl. .................................................. 424/200
[58] Field of Search ......................................... 424/200

[56] References Cited

U.S. PATENT DOCUMENTS 3,244,586  4/1966  Rigterink ........................... 424/200

OTHER PUBLICATIONS

Chemical Abstracts 78:93577s (1973).

*Primary Examiner*—Leonard Schenkman
*Attorney, Agent, or Firm*—Curtis, Morris & Safford

[57] ABSTRACT

Pesticidal compositions containing a combination of 1-phenyl-3-(O,O-diethylthionophosphoryl)-1,2,4-triazole (I) (=triazophos) and O,O-diethyl-O-3,5,6-trichloro-2-pyridyl-phosphorothioate (II) (=chloropyrifos) at a weight ratio of preferably 1:10 to 10:1 are disclosed. These pesticidal compositions exhibit synergistic activity in particular against insects and acarides.

9 Claims, No Drawings

PESTICIDAL COMPOSITIONS

The present invention relates to pesticidal compositions, in particular insecticides and acaricides, that are characterized by a content of (I) 1-Phenyl-3-(O,O-diethylthionophosphoryl)-1,2,4-triazole (common name: triazophos) in combination with (II) O,O-diethyl-O-3,5,6-trichloro-2-pyridyl-phosphorothioate (common name: chloropyrifos).

Compound I (triazophos) of formula I

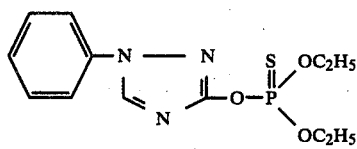

is known to be a very effective insecticide and acaricide against sucking and biting insects and red spider mites as well as against nematodes (cf., for example Vulic, M. et al., VII Int. Congr. Plant Protection, Paris, 1970, page 123 (abstr.))

It is used especially for combatting pests in cotton, rice, citrus fruits, fruit and vegetable cultures.

Compound II (chloropyrifos) of formula II

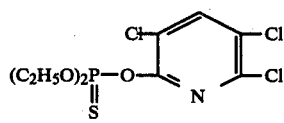

is likewise a known insecticide that is very effective against biting and sucking insects (cf., for example U.S. Pat. No. 3,244,586). This insecticide is used especially for combatting pests in the household, or for combatting terriclous pests and leaf eating harmful organisms in plant cultures.

In some cases, however, a satisfactory effectiveness against pests of interest in said cultures or application fields cannot be achieved when using the compounds I and II individually.

For example, when using compound I (triazophos) in low concentrations for economical reasons and with a view toward pest control exhibiting as little polluting effect as possible, it is no longer sufficiently effective against a number of biting insects. Compound II (chloropyrifos), when used alone, is not sufficiently effective against a number of sucking insect pests and against red spider mites.

It has now been found that a combination of triazophos and chloropyrifos is distinguished by a synergistic activity, in particular against insects and acarides. The mixture ratio of triazophos to chloropyrifos may be in the range of from 1:10 to 10:1, preferably of from 1:1 to 10:1.

The pesticidal compositions prepared according to the present invention from combinations of said active ingredients, as compared to compositions containing only the individual active components in corresponding amounts, are distinguished by an improved synergistic effectiveness, in particular against insects and acarides. Therefore, the combinations of active ingredients according to the present invention can be used in much lower concentrations and still exhibit the same insecticidal and acaricidal effect as that obtained with the respective single components. The combinations of active ingredients can therefore be used in a number of application fields to combat important pests successfully. For example, they are suitable for combatting leptidopterae, in particular *Spodoptera littoralis*, Heliothis spp., in cotton, citrus fruits and vegetable cultures and in crop and wine cultures. They can moreover be used to combat successfully red spider mites in said cultures.

The mixtures of active ingredients according to the invention can be used in the form of the usual formulations such as emulsion concentrates, ULV solutions, dispersions, wettable powders, dusts or granules. In general the formulations contain from about 10 to 90 weight % of active ingredients. In addition, they may contain the usual adhesives, emulsifiers, wetting agents, dispersing agents, fillers and carriers. Tank mixtures consisting of the individual active components at adequate mixing ratios may be used alternatively in practice. If desired, the individual components may alternatively be applied in subsequent steps. Emulsifiable concentrates are obtained by dissolving the active ingredients in suitable organic solvents, for example toluene, xylenes, chlorobenzenes and other aromatic compounds of high boiling point; petrols or paraffin oils; cyclohexanone, dimethylformamide, dimethylsulfoxide, tetrahydrofuran, dioxan, diacetonyl alcohol, ethyl acetate and isophorone.

With "Ultra-Low-Volume" (ULV) formulations, there are suitably used solvents of high boiling point to minimize loss due to evaporation during application by spraying. Examples of such solvents are high boiling paraffin oils, ketones or esters and vegetable oils.

Suitable carrier materials for solid formulations are in particular mineral substances such as silicic acids and silicates such as diatomaceous earth, kaolins, alumina or talc, chalk or siliceous chalk; or formulations of these mineral substances with additives such as stearates, alkyl-, aryl- or alkylarylsulfonates, lignosulfonates and the like. Moreover, there may be used further wetting agents, dispersing agents and adhesives or most different kinds of grinding auxiliaries, depending on the intended application.

Prior to use, said emulsion concentrates, wettable powders or dispersions are diluted with a suitable diluent and thus brought to a concentration suitable for their use in practice. This concentration varies, depending on the indended application and on the climatic conditions, in particular temperature and humidity, and is generally of from 0.005 to 1.0 weight % of portion of total active ingredients, for example with wettable powders.

The pesticidal compositions according to the invention exhibit an outstanding effectiveness against insect pests as well as against acarides and may be used successfully in far lower quantities or concentrations than pesticidal compositions that contain only one of both active ingredients alone.

The following examples illustrate the invention:

FORMULATION EXAMPLES

Example 1

Emulsion concentrate (weight ratio of triazophos to chloropyrifos = 10:1)

4.0 weight parts of chloropyrifos
40.0 weight parts of triazophos 5.0 weight parts of calcium dodecyl benzenesulfonate
7.4 weight parts of castor oil polyglycol ether (40 EO)+)
1.6 weight parts of tributylphenyl polyglycol ether (50 EO)
42.0 weight parts of xylene
(+) number of EO=number of ethylene oxide units in polyglycol ether molecule.

Example 2

Emulsion concentrate (weight ratio of triazophos to chloropyrifos=1:10)
40.0 weight parts of chloropyrifos
4.0 weight parts of triazophos
3.0 weight parts of calcium dodecyl benzenesulfonate
2.0 weight parts of castor oil polyglycol ether (36 EO)
51.0 weight parts of xylene.

Example 3

A tank mixture is obtained by mixing triazophos (I) in the form of an emulsion concentrate containing 40 weight % of active ingredient and chloropyrifos (II) in the form of a wettable powder containing 50 weight % of active ingredient, at a ratio of I:II of 1:1, in an amount such that in the ready to use spray liquor the concentration of the mixture of active ingredients (I+II), depending on the requirements imposed by the method of application and by the plant culture, is in the range of from about 0.2 to 5.6 weight %.

BIOLOGICAL EXAMPLES

Example 4

Larvae of the cotton pest *Spodoptera littoralis* BOISB. in the third stage of development and their feed (leaves of Phaseolus vulgaris) were sprayed separately dripping-wet in a laboratory with the active ingredients or combinations of active ingredients specified in Table 1 and which had been emulsified or suspended in water, at the concentrations specified in the table (weight %).

After drying of the coating applied by spraying, the treated larvae were put on the treated and dried leaves.

The effect of the active ingredients or of mixtures thereof was determined after 3 hours (initial effect) of after 48 hours and was found to be as indicated in Table 1.

TABLE 1

1.1 Mixing ratio of compounds I:II = 1.9:1 (weight parts)

| Treatment with | Concentration of active ingredients (weight %) | Killing rate in % after 3 hours |
|---|---|---|
| Compound I | 0.0024 | 10 |
| Compound II | 0.001248 | 15 |
| Compound I<br>+<br>Compound II | 0.0024<br>+<br>0.001248 | 75 |

1.2 Mixing ratio of compounds I:II = 1.7:1 (weight parts)

| Treatment with | Concentration of active ingredients (weight %) | Killing rate in % after 48 hours |
|---|---|---|
| Compound I | 0.00012 | 0 |
| Compound II | 0.000072 | 5 |
| Compound I<br>+<br>Compound II | 0.00012<br>+<br>0.000072 | 30 |

1.3 Mixing ratio of compounds I:II = 3.3:1 (weight parts)

TABLE 1-continued

| Treatment with | active ingredients (weight %) | Killing rate in % after 48 hours |
|---|---|---|
| Compound I | 0.00012 | 0 |
| Compound II | 0.000036 | 0 |
| Compound I<br>+<br>Compound II | 0.00012<br>+<br>0.000036 | 70 |

1.4 Mixing ratio of compounds I:II = 1:1.2 (weight parts)

| Treatment with | Concentration of active ingredients (weight %) | Killing rate in % after 48 hours |
|---|---|---|
| Compound I | 0.00012 | 0 |
| Compound II | 0.000144 | 5 |
| Compound I<br>+<br>Compound II | 0.00012<br>+<br>0.0000144 | 40 |

Example 5

Cotton plants were sprayed in the open field with the active ingredients or combinations of active ingredients specified in Table 2, which are emulsified or suspended in water, with the quantities specified in the table (kg of active ingredient (AI) per hectar). After drying of the coating applied by spraying the leaves were collected and fed to larvae of Spodoptera littoralis BOISD. in the second ($=L_2$) and in the fourth ($=L_4$) stage of development, in the laboratory. Evaluation was done for the first time after 24 hours. A second evaluation took place after a further 24 hours. The result (in % of animals killed) is summarized in Table 2.

TABLE 2

| Treatment with | Quantity of active ingredient kg of AI per ha | % of killed animals after | | | |
|---|---|---|---|---|---|
| | | 24 hrs | | 48 hrs | |
| | | $L_2$ | $L_4$ | $L_2$ | $L_4$ |
| 2.1 Mixing ratio of compounds I:II = 1.4:1 (weight parts) | | | | | |
| Compound I | 0.84 | 0 | 0 | 0 | 0 |
| Compound II | 0.6 | 0 | 0 | 0 | 0 |
| Compound I<br>+<br>Compound II | 0.84<br>+<br>0.6 | 80 | 70 | 100 | 100 |
| 2.2 Mixing ratio of compounds I:II = 1.6:1 (weight parts) | | | | | |
| Compound I | 0.84 | 0 | 0 | 0 | 0 |
| Compound II | 0.72 | 5 | 0 | 5 | 0 |
| Compound I<br>+<br>Compound II | 0.84<br>+<br>0.72 | 90 | 80 | 100 | 100 |
| 2.3 Mixing ratio of compounds I:II = 1:1 (weight parts) | | | | | |
| Compound I | 0.84 | 0 | 0 | 0 | 0 |
| Compound II | 0.84 | 10 | 5 | 10 | 5 |
| Compound I<br>+<br>Compound II | 0.84<br>+<br>0.84 | 100 | 80 | 100 | 100 |
| 2.4 Mixing ratio of compounds I:II = 1:1.14 (weight parts) | | | | | |
| Compound I | 0.84 | 0 | 0 | 0 | 0 |
| Compound II | 0.96 | 15 | 10 | 17 | 14 |
| Compound I<br>+<br>Compound II | 0.84<br>+<br>0.96 | 100 | 100 | 100 | 100 |
| 2.5 Mixing ratio of compounds I:II = 10:1 (weight parts) | | | | | |
| Compound I | 1.2 | 10 | 5 | 20 | 8 |
| Compound II | 0.12 | 0 | 0 | 0 | 0 |
| Compound I<br>+<br>Compound II | 1.2<br>+<br>0.12 | 60 | 45 | 80 | 70 |
| 2.6 Mixing ratio of compounds I:II = 1:10 | | | | | |

TABLE 2-continued

| Treatment with (weight parts) | Quantity of active ingredient kg of AI per ha | % of killed animals after | | | |
|---|---|---|---|---|---|
| | | 24 hrs | | 48 hrs | |
| | | $L_2$ | $L_4$ | $L_2$ | $L_4$ |
| Compound I | 0.07 | 0 | 0 | 0 | 0 |
| Compound II | 0.7 | 15 | 5 | 6 | 5 |
| Compound I + Compound II | 0.07 + 0.7 | 50 | 45 | 65 | 70 |

What is claimed is:

1. An insecticidal composition, containing as active ingredient, insecticidally effective amounts of (I) 1-Phenyl-3-(O,O-diethylthionophosphoryl)-1,2,4-triazole and (II) O,O-diethyl-O-3,5,6-trichloro-2-pyridyl-phosphorothioate wherein the proportion by weight of component (I) to component (II) is in the range of from 1:10 to 10:1.

2. The insecticidal composition as defined in claim 1 wherein the proportion by weight of component (I) to component (II) is in the range of from 1:1 to 10:1.

3. An insecticidal composition containing from 0.005% to 90% by weight of the active ingredient as defined in claim 1 in admixture with up to 99.995% by weight of a suitable formulation auxiliary.

4. An insecticidal composition containing from 0.005% to 90% by weight of the active ingredient as defined in claim 2 in admixture with up to 99.995% by weight of a suitable formulation auxiliary.

5. A method for combatting leptidopterae in plants which comprises applying to an infested area an effective amount of an insecticidal composition as defined in claim 1.

6. A method for combatting leptidopterae in plants which comprises applying to an infested area an effective amount of an insecticidal composition as defined in claim 3.

7. A method for combatting leptidopterae in cotton plants, citrus fruits, vegetable cultures, crop cultures or wine cultures which comprises applying to the infested area an effective amount of an insecticidal composition as defined in claim 1.

8. A method for combatting leptidopterae in cotton plants, citrus fruits, vegetable cultures, crop cultures or wine cultures which comprises applying to the infested area an effective amount of an insecticidal composition as defined in claim 2.

9. The method of claim 7 or 8 wherein the insects are *Spodoptera littoralis*.

* * * * *